United States Patent [19]

Richards

[11] Patent Number: 5,306,142
[45] Date of Patent: Apr. 26, 1994

[54] CRIMPABLE ORTHODONTIC HOOK

[75] Inventor: Cecil J. Richards, Kouts, Ind.

[73] Assignee: TP Orthodontics, Inc., Westville, Ind.

[21] Appl. No.: 927,929

[22] Filed: Aug. 7, 1992

[51] Int. Cl.$^5$ ............................................. A61C 3/00
[52] U.S. Cl. .......................................... 433/22; 433/17
[58] Field of Search ................... 433/4, 5, 7, 8, 9, 10, 433/11, 16, 17, 18, 19, 22

[56] References Cited

U.S. PATENT DOCUMENTS

| | | | |
|---|---|---|---|
| 3,158,934 | 12/1964 | Waldman. | |
| 3,164,900 | 1/1965 | Wallshein | 433/13 |
| 3,639,986 | 2/1972 | Kesling | 433/17 |
| 3,916,526 | 11/1975 | Schudy | 433/17 X |
| 3,964,165 | 6/1976 | Stahl | 433/8 |
| 4,202,100 | 5/1980 | Forster | 433/7 |
| 4,639,219 | 1/1987 | Gagin | 433/22 |
| 4,797,095 | 1/1989 | Armstrong et al. | 433/22 |
| 4,799,883 | 1/1989 | Stoller et al. | 433/11 X |

OTHER PUBLICATIONS

"Product News for Orthodontists", GAC International, Inc., vol. 4, No. 1.
Unitek Corporation catalog, pp. 90–92 (1973).
American Orthodontics Corporation catalog, p. 85 (1989).
Ortho Organizers brochure (1986).
Journal of Clinical Orthodontics ad (Mar., 1982).

*Primary Examiner*—Gene Mancene
*Assistant Examiner*—Nicholas D. Lucchesi
*Attorney, Agent, or Firm*—Lloyd L. Zickert

[57] ABSTRACT

An improved orthodontic device defining an anchor for an elastic, ligature or spring along an archwire or a stop on a wire member, which includes a crimpable hook or stop having a tubular body with inner wire-engaging surfaces coated with an abrasive material to produce an anti-sliding and anti-rotating engagement with the wire when crimped down upon the wire.

13 Claims, 3 Drawing Sheets

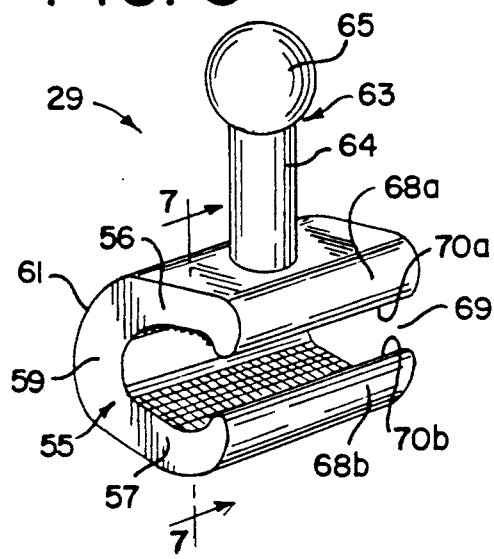
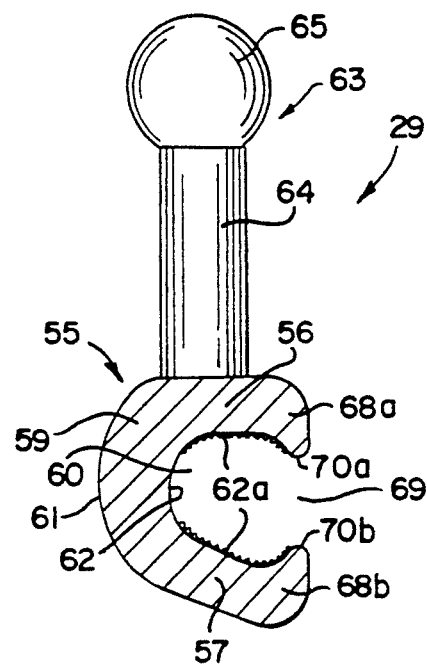
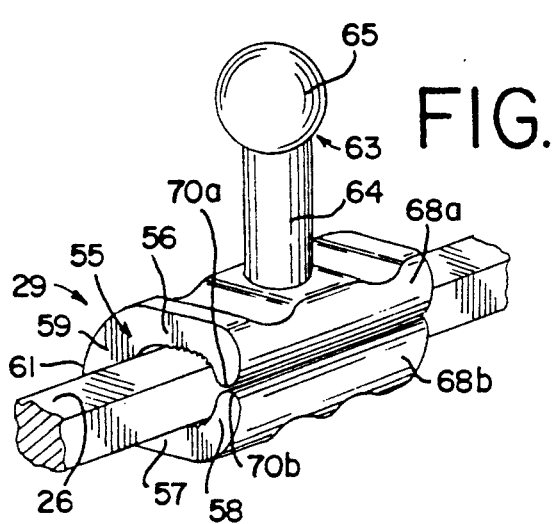
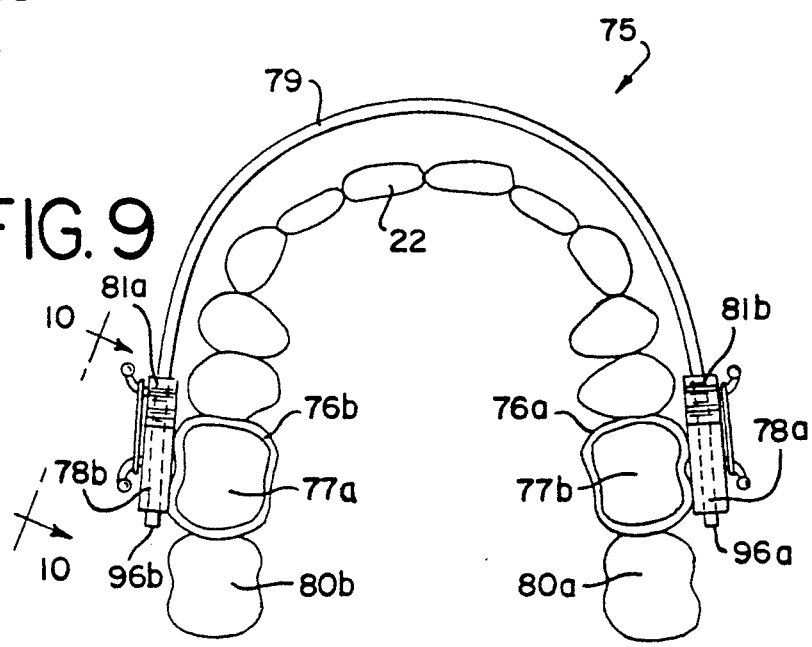

5,306,142

CRIMPABLE ORTHODONTIC HOOK

DESCRIPTION

This invention relates in general to an improved orthodontic device, and more particularly to a crimpable member or body mountable on an archwire or wire, wherein the inner surfaces of the crimpable member which contact the archwire are coated with an abrasive material to increase friction and resist slippage along the archwire when the crimpable member is crimped down on the archwire, and still more particularly to a crimpable hook or stop including a crimpable member or body having inner surfaces coated with an abrasive material which are crimped down upon the wire.

BACKGROUND OF THE INVENTION

Heretofore, it has been well known to provide orthodontic crimpable hooks and stops/spacers which may be adjustably positionable on an archwire or other orthodontic wire for a variety of uses. For example, crimpable ball hooks which are mounted on orthodontic archwires are commonly used for intermaxillary fixation during orthodontic and/or surgical treatment. Another example which is well known is to provide orthodontic crimpable stops that are adjustably positionable on a lip bumper or a face bow wire member. Exemplary of some of these types of mechanisms heretofore known are disclosed in U.S. Pat. No. 4,639,219, which provides a comprehensive background on the use of crimpable ball hooks.

A crimpable ball hook includes a crimpable member or body for receiving an orthodontic archwire and a ball hook extending from the crimpable member, as shown and described in U.S. Pat. No. 4,639,219. The crimpable member may be closed and slidable over an end of the archwire or open and applied to any part of the archwire. Both types of crimpable members are adjustably positionable along the archwire. Even when these crimpable bodies are crimped, they tend to slide along the archwire when forces are applied to them. This is considered a disadvantage or problem by some orthodontists who would prefer the crimpable ball hook to remain in a fixed location on the archwire at all times. Thus, all known crimpable or collapsible hooks and/or stops suffer from a lack of adequate friction to keep them from sliding along the wire even when they are forcibly crimped onto the wire.

SUMMARY OF THE INVENTION

The present invention overcomes the relatively low friction problem heretofore known by providing an auxiliary hook or stop wherein the inner surfaces of the crimpable body are coated with an abrasive material. This abrasive coating, which may be applied to all or part of the inner surface, engages the archwire when the hook or stop is crimped, thereby significantly increasing the friction between the hook or stop and the wire, after crimping, to a level that resists sliding along and rotating on the wire. The abrasive coating which is applied to all or selected portions of the inner surface of the crimpable body may be a layer of suitable carborundum. It may be applied by a suitable coating device such as the Rocklinizer TM device made by Rocklin Mfg. Co., the D-Gun TM device made by Union Carbide Corporation, or any other coating device. Rocklinizer TM is a trademark owned by Rocklin Mfg. Co. and D-Gun TM is a trademark owned by Union Carbide Corporation. The coating of carborundum defines a surface that when in firm engagement with the archwire inhibits relative sliding movement.

It is therefore an object of the present invention to provide an improved crimpable orthodontic device for mounting on an orthodontic archwire or wire member which resists sliding along the wire when it is crimped and when subjected to forces along the wire.

Another object of the present invention is to provide an improved crimpable hook for placement on an orthodontic archwire which remains fixed in position when it is crimped on the archwire and thereafter subjected to forces along or around the archwire.

Another object of the present invention is to provide an improved orthodontic split crimpable hook for placement on an orthodontic archwire which has been mounted on the teeth which remains fixed in position when it is crimped on the archwire against forces that would tend to slide it along or rotate it about a round archwire.

Another object of the present invention is to provide an improved orthodontic crimpable stop or spacer for mounting on an archwire, a lip bumper or a face bow which remains fixed in position when crimped.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 6 is an enlarged perspective view of a crimpable hook according to the invention having a split body and in the form prior to mounting and illustrating the abrasive coating on the inner surfaces of the split crimpable body;

FIG. 7 is a further enlarged cross-sectional view of the split crimpable body of the crimpable hook taken substantially along line 7—7 of FIG. 6 and further illustrating the abrasive coating on the inner surface of the split crimpable body;

FIG. 8 is a perspective view of the crimpable ball hook in FIG. 6 shown mounted on a section of archwire with the split crimpable body closed and the indentations from crimping on the outer surface of the body;

FIG. 9 is a top plan view of a dental arch having a crimpable stop of the present invention shown mounted on a lip bumper received in buccal tubes;

DESCRIPTION OF THE INVENTION

Figure 1:
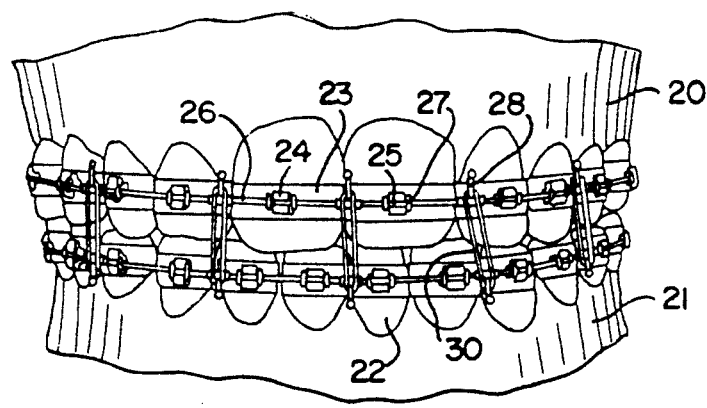
FIG. 1 is a front elevational view of the upper and lower dental arches having orthodontic brackets mounted on the teeth, archwires secured in the brackets, and the crimpable ball hooks of the present invention mounted on the archwires together with elastics connected to the ball hooks to provide intermaxillary fixation.

Referring to the drawings, and specifically to FIG. 1, the upper dental arch 20 and the lower dental arch 21 of a person are shown in a closed position, whereby the teeth 22 of both arches are in the desired occlusion. Each tooth 22 on both arches has a band 23 suitably cemented around it. An orthodontic edgewise bracket 24 is affixed to each band at the labiobuccal side of the tooth. It should be noted that it is also well known in the art to bond an orthodontic bracket directly to a tooth. Each bracket 24 has a mesiodistally extending substantially rectangular slot 25 for receiving an archwire 26. Two archwires, one for the upper arch 20 and one for the lower arch 21, are serially secured in the respective slots of the brackets by suitable ligatures 27.

The crimpable hook 28 of the present invention is mounted on the archwire, between two adjacent brackets, prior to or subsequent to placement of the archwire in the brackets. If mounted prior to placement, a crimpable hook 28, which is peripherally closed as illustrated in FIGS. 2 through 5, can be used; if mounted subsequent to placement, a peripherally split crimpable hook 29, as illustrated in FIGS. 6 through 8, can be used.

Figure 2:
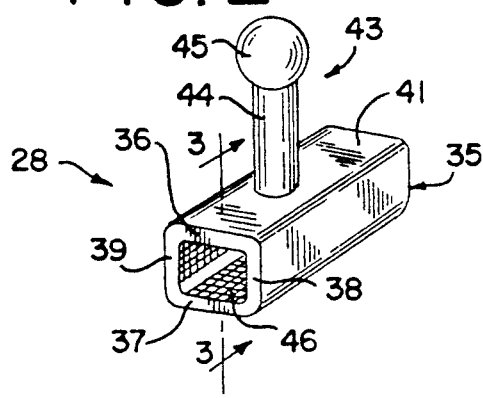
FIG. 2 is an enlarged perspective view of the crimpable ball hook according to the invention prior to mounting and illustrating the abrasive coating on the inner surfaces of the crimpable member or body.
Figure 3:
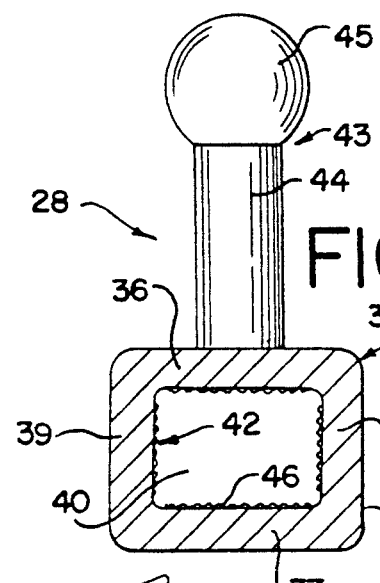
FIG. 3 is a further enlarged cross-sectional view of the crimpable tubular body of the crimpable hook taken substantially along line 3—3 of FIG. 2 and further illustrating the abrasive coating on the inner surfaces of the crimpable body.

The crimpable hook 28, as further illustrated in FIGS. 2 and 3, has a substantially rectangular or channel-shaped closed tubular member or body 35 with four connected walls or sides for use on rectangular wire. The tubular member includes a gingival side or wall 36, an occlusal side or wall 37, a lingual side or wall 38, and a labiobuccal side or wall 39. These walls define an archwire opening 40 for receiving an archwire in the tubular member 35. The four walls of the tubular member 35 form an outer smooth surface 41 and an inner surface 42. It should be appreciated that the lingual wall 38 and the labiobuccal wall 39 could be reversed without affecting the function of the crimpable hook 28.

A hook 43 extends from the gingival wall and includes a shaft or stem 44 and a ball or rounded head 45. The shaft 44, which is integrally attached to the gingival side 36 of the tubular member 35, extends from the tubular member in a substantially perpendicular relationship. At the end of shaft 44 is the integrally attached ball or ball-shaped head 45. It may also be appreciated the stem may terminate with merely a blunt end. This hook 43, having a shaft and a ball combination, functions as an anchor or hook around which a ligature or elastic 30 may be looped, as shown in FIG. 1. It should be appreciated that the hook need not have a ball or other protuberance on its end to function properly.

In one application, and as illustrated in FIG. 1, two crimpable hooks 28, one on the archwire of the upper dental arch 20 and one on the archwire of the lower dental arch 21, are placed so they substantially directly oppose one another. Ligatures 30 are hooked on the opposite extending crimpable hooks to connect the archwires and to hold the upper and lower dental arches together in occlusion. The combination of several of these opposing pairs of crimpable hooks attached by ligatures can be used to achieve intermaxillary fixation following orthognathic surgery.

Also a rubber band can be placed by the patient or orthodontist over the crimpable hook and around a hook attached to the teeth and/or archwires in the same or opposing arch to promote orthodontic tooth movements. It should be appreciated that the shape of the tubular member and the hook can vary in keeping with the present invention.

The inner surface 42 of the tubular member is applied entirely or at selective areas with an abrasive layer or coating 46. Preferably, the abrasive coating is only on the inside walls and not at the corners. This abrasive material or layer may be applied by a suitable coating device, such as the Rocklinizer ™ device, which deposits carborundum on the inner surface 42. More specifically, the Rocklinizer ™ device electronically impregnates and deposits wear-resistant material, such as tungsten carbide or titanium carbide, to metallic surfaces. This process is advantageous because it minimizes electrode consumption and because after using the Rocklinizer device, no heat-treating, grinding, or other surface treatment is necessary. Similarly, the D-Gun ™ device may be used to apply the layer of carborundum on the inner surface of the crimpable member. It will also be appreciated that an abrasive coating may be applied to the inner surface of the crimpable member by various other electronic, chemical, or physical methods which are customary in the industry.

Figure 4:
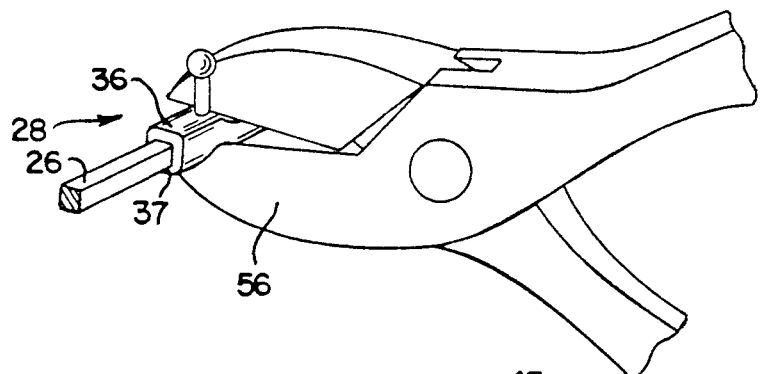
FIG. 4 is a perspective view of the crimpable hook shown mounted on a section of archwire and further illustrating wire cutters which may be used to crimp the crimpable body of the hook onto the archwire.
Figure 5:
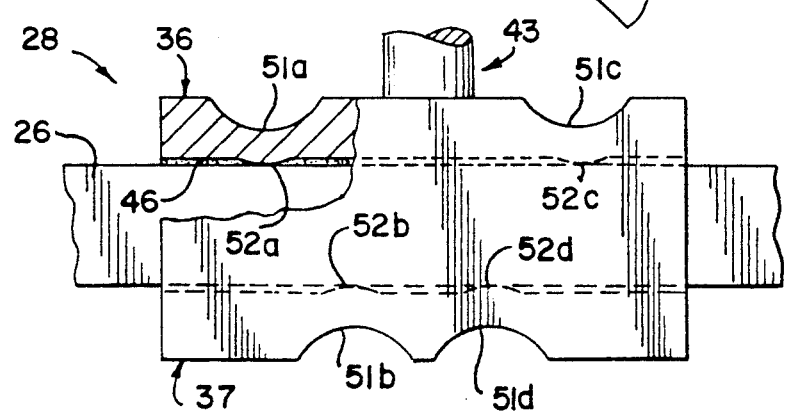
FIG. 5 is an enlarged fragmentary front view of the crimpable hook shown mounted on a section of archwire with a portion of the crimpable body of the hook broken away to illustrate an indentation in the crimpable body and engagement between the abrasive coating and the archwire.

The function of the abrasive material on the inner surfaces of the crimpable tubular member is best illustrated in FIGS. 4 and 5. FIG. 4 illustrates the crimpable hook 28 of the present invention with an archwire 26 received in the archwire opening 40 of the tubular member 35. A standard pair of wire cutters 50 is shown in position for crimping the gingival side 36 and the occlusal side 37 of the tubular member 35. Wire cutters, as illustrated, or other crimping devices can be used for crimping the tubular member on the archwire. The tubular member should be crimped on opposite sides to positively secure it to the archwire. It should be appreciated that the tubular member may be crimped on the mesial and/or distal ends adjacent to the hook 43.

FIG. 5 further illustrates the crimpable hook 28 after it is crimped onto the archwire 26. The tubular member has two opposing depressions or crimps 51a and 51b on one side of the ball hook 43 and two opposing depressions or crimps 51c and 51d on the other side of the ball hook, crimps 51a and 51c being on the gingival side 36 and crimps 51b and 51d being on the occlusal side 37. As illustrated in FIG. 5, the abrasive coating 46 engages the archwire at contact points 52a, 52b, 52c and 52d, corresponding respectively to the crimps 51a, 51b, 51c and 51d of the tubular member. As shown, the opposing crimps are offset as it would be normal for the person performing the crimping to place one jaw of the crimping pliers against one side of the hook and then tilt the jaws to assure the other jaw is aligned with the tubular member and not off the end to engage the archwire.

Similarly, when crimping at the other side of the hook, the jaws will normally be tilted to offset the crimps and produce a crimping pattern like that illustrated in FIG. 5. However, the crimps may be directly opposed and still function in the same manner.

The engagement of the archwire and the abrasive coating on the inner surface of the member at these contact points significantly increases the friction on the archwire to a sufficient level to inhibit the tubular member from sliding along and rotating on the archwire. Thus, the crimpable hook will substantially remain in the fixed location when the hook is crimped onto the archwire.

Referring now to FIGS. 6 to 8, a second embodiment of the invention, the split crimpable hook 29, is illustrated. FIGS. 6 and 7 show the hook prior to mounting, while FIG. 8 shows the hook in mounted and crimped position on the archwire 26. Unlike the crimpable hook 28 with a closed tubular body, the split crimpable hook 29 has a split tubular body or channel member 55 with a gingival side or wall 56, an occlusal side or wall 57, a lingual side or wall 58, and a labiobuccal side or wall 59 which define an archwire opening 60. The channel member 55 also has an outer surface 61 and an inner surface 62. Preferably, only that part of the inner surface at opposed walls 56 and 57 include an abrasive layer 62a, as these surface areas are crimped against the archwire.

The lingual side 58 is divided into two segments 68a and 68b, leaving a gap 69 at least slightly larger than the archwire to allow the channel member 55 to be mounted at any location on an archwire after the archwire is attached to the brackets. Each of these segments 68a and 68b of the lingual side 58 has an edge, 70a and 70b respectively, which are constructed to lock around the archwire when the channel member is properly crimped on an archwire.

The labiobuccal side 59 has a greater width and a more rounded outer surface 61 than the outer surface 41 of the tubular member 35. This modified construction provides increased structural integrity for the channel member, especially during the bending and crimping process.

Similar to the hook 43, the hook 63 has a shaft 64 which extends in a substantially perpendicular relationship from the gingival side 56. Integral with the end of the shaft 63 is a ball-shaped knob or head 65. Together, the shaft 64 and the ball-shaped knob 65 function as an anchor for a ligature. However, it should be appreciated that the end of the shaft can be merely rounded, spherical or ball-shaped, or of any suitable shape and dimension as long as it is smooth to avoid sharp edges in the mouth, and as long as a ligature can be securely anchored to it.

The split crimpable hook 29 is further illustrated in FIG. 8 after being crimped onto an archwire 26. The tubular member 65 in FIG. 8 has been crimped such that the gingival side 56 and the occlusal side 57 are in a more parallel relationship and the edges 70a and 70b of the lingual side are in substantially abutting relationship to each other. The abrasive material on the inner surfaces of the channel member frictionally engages the archwire at the contact points under the crimps in the same manner as the crimps in the embodiment of FIGS. 1 to 5, thereby preventing the crimpable hook 29 from sliding along the archwire. Also, the crimps may be offset as shown or in directly opposed relation as the embodiment of FIGS. 1 to 5.

Referring now to FIG. 9, a lip bumper 75 is shown mounted on the teeth 22 of the lower dental arch. More specifically, a band 76a is mounted on the first molar 77a on the right side of the arch and a band 76b is mounted on the first molar 76b on the left side of the arch. Attached to each band is a buccal tube, 78a and 78b, respectively, having at least one opening for receiving the distal ends 96a and 96b of the wire member 79 of the lip bumper and through which the wire member slides. The wire member 79 is received in the buccal tubes 78a and 78b.

The most labial part of the wire member 79 contacts the bottom lip on the inside of the mouth (not shown). When the lip moves lingually, it applies force on the wire member at the most labial point. This force tends to move the wire member 79 in a distal direction on both sides of the arch. As the wire member moves distally, it slides distally through the buccal tubes. However, to accomplish the ultimate goal of moving the first and second molars 77a, 77b and 80a, 80b, respectively, in a distal direction, this force or movement of the wire member must be transferred to the buccal tubes. Upon transfer of this movement or force, the buccal tubes will move the first and second molars in a distal direction.

Crimpable orthodontic stops 81a and 81b of the present invention will facilitate this transfer of force. The crimpable orthodontic stop 81a, as more clearly illustrated in FIGS. 10 and 11, includes a closed tubular member 82 which has a smooth outer surface 83 and an inner surface 84. At least portions of the inner surface 84, preferably near each end, have an abrasive coating 85 similar to the abrasive coating on the crimpable hooks. When the orthodontic stop is crimped, the abrasive coating 85 engages the wire member 79, thereby increasing the friction between the stop and the wire member. This increased friction is sufficient to fix the crimpable orthodontic stop 81a on the wire member 79 at the position where it is crimped.

When both crimpable orthodontic stops 81a and 81b are crimped in place and the wire member 79 is forced distally by the lip, the stops, which are in abutting relation with buccal tubes 78a and 78b, will also apply a distal force to the buccal tube. Specifically, the wire member is unable to slide through the buccal tubes because the stops are abutting the mesial sides 86 of the buccal tubes. At that point, the distal force from the wire member transfers to the buccal tubes via the stops. Each buccal tube, being securely attached to the first molar by way of the band, applies distal forces to the first molar urging its movement in a distal direction. As seen in FIG. 9, the stops 81a and 81b, respectively, abut buccal tubes 78a and 78b to apply distal forces to the first molars 77a and 77b.

Figure 10:
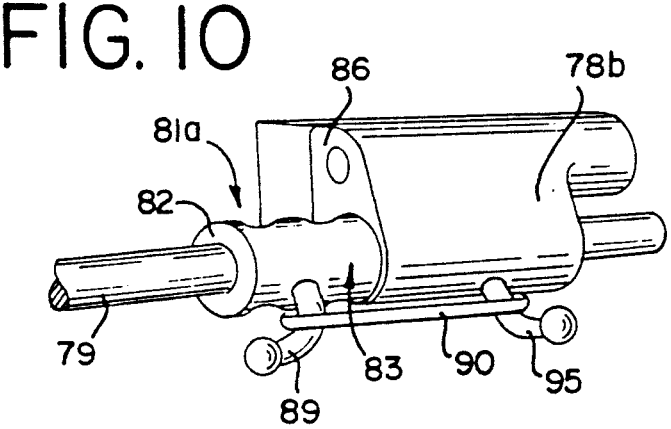
FIG. 10 is an enlarged perspective view of the crimpable stop and the buccal tube of FIG. 9 taken substantially along line 10—10 thereof.
Figure 11:
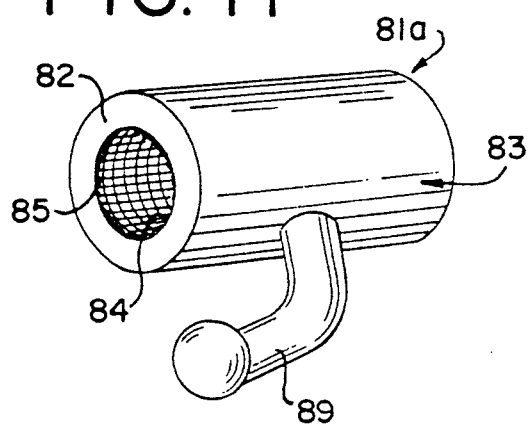
FIG. 11 is a perspective view of the crimpable stop of FIG. 9 prior to being mounted for use and illustrating the abrasive coating on the inner surface of the tubular body.

As illustrated in FIGS. 10 and 11, a mesially extending hook 89 may be included on the stops for connecting the stop to the buccal tube. A distally extending hook 95 may be mounted on the buccal tube 78, and a suitable ligature 90 may be hooked over the hooks 89 and 95 to connect the stop to the tube 78 to hold the stop against the tube. Thus, a stop may optionally include a hook, and the hook may optionally include a rounded or balled end.

Figure 12:
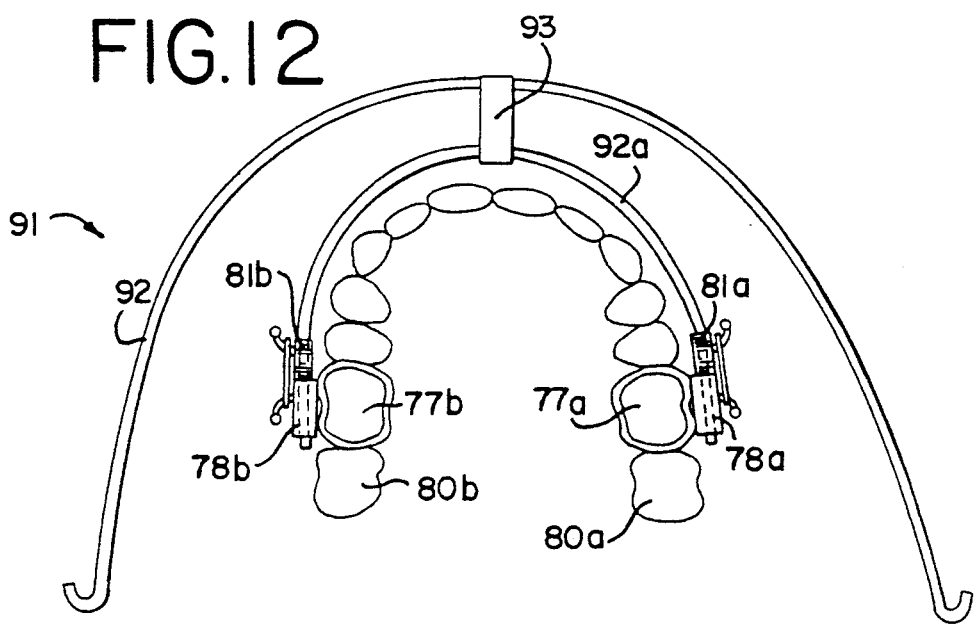
FIG. 12 is a top plan view of a dental arch having a crimpable stop mounted on the inner bow of a face bow received in buccal tubes.

A further use of the crimpable orthodontic stop 81 is illustrated in FIG. 12 where a conventional face bow 91 of a headgear apparatus is shown mounted on headgear tubes. The headgear 91 has an outer bow 92 and an inner bow 92a. The outer bow 91 is connected to the inner bow 92a by a connecting link 93. In practice, the entire face bow is urged toward the back of the patient's head by suitable headgear to apply distal forces to the molars. Stops 81a and 81b with abrasive on their inner surfaces are respectively crimped onto the distal ends of the inner bow to abut and apply pressure to the buccal or headgear tubes 78a and 78b to move the molars distally. Thus, it will be appreciated that the stops can be adjustably crimped along the lip bumper or face bow to a desired position for easily fitting the appliances to a patient's arch.

While the stops 81 include closed tubular members, it should be appreciated that they could have a split tubular form like the split crimpable hook of FIGS. 6 to 8. It may be further appreciated that a rubber band may be placed by the patient or the orthodontist over a crimpable hook and over a hook suitably attached to a tooth and/or archwire in the same or opposing arch to promote orthodontic tooth movement. It should be further appreciated the tubular member of the crimpable hook may be cylindrically shaped for use on round wire if desired, although orientation of the hook is more easily established with a generally rectangular tubular member mounted on rectangular wire.

The crimpable hooks and stops may be cast stainless steel where the tubular member is integrally cast with the hook. Further, they may be made in two parts and assembled, where the tubular member is formed, the hook is formed and then soldered or brazed to the tubular member. When made in two parts and assembled, the tubular member may be made of a softer metal than the hook so that it may be more easily crimped.

It will be understood that modifications and variations may be effected without departing from the scope of the novel concepts of the present invention, but it is understood that this application is to be limited only by the scope of the appended claims.

The invention is hereby claimed as follows:

1. An orthodontic crimpable hook adapted to be mounted on an archwire and used for inter or intra arch traction comprising, a tubular member defining an opening for receiving said archwire, said member having a hook extending from said member and inner surfaces for contacting the archwire, an abrasive coating on at least part of said inner surfaces of said member, said member being crimpable such that upon crimping on said archwire said abrasive coating on said inner surfaces of said member engages said archwire to increase the friction between said member and said archwire.

2. An orthodontic hook as defined in claim 1, wherein said member is peripherally closed and mountable on said archwire prior to positioning of said archwire.

3. An orthodontic hook as defined in claim 1, wherein said member is peripherally split and mountable on said archwire subsequent to positioning of said archwire in the mouth.

4. An orthodontic hook as defined in claim 1, wherein said abrasive material on said inner surfaces of said member is carborundum.

5. An orthodontic hook as defined in claim 1, wherein said hook includes a stem extending from said tubular member.

6. An orthodontic hook as defined in claim 5, wherein the outer end of the stem includes an enlarged head.

7. An orthodontic hook as defined in claim 6, wherein the head is ball-shaped.

8. An orthodontic hook as defined in claim 1, wherein said tubular body is rectangular in cross section and adapted to be used on rectangular wire.

9. A crimpable orthodontic stop adapted to be mounted on the wire of a lip bumper or face bow, said stop including a tubular member having an inner surface defining an opening for receiving the wire, an abrasive coating on the inner surface of said tubular member, said member being crimpable such that upon being crimped on the wire said inner surface of said tubular member engages said wire with sufficient friction that said orthodontic stop resists sliding along the wire.

10. An orthodontic stop as defined in claim 9, wherein said tubular body is cylindrical.

11. An orthodontic stop as defined in claim 9, wherein said stop comprises a channel that is open on one side.

12. An orthodontic stop as defined in claim 9, wherein said abrasive coating on said inner surface of said tubular body is a layer of carborundum.

13. A crimpable orthodontic hook which is adapted to be mounted on an archwire and used for intermaxillary traction comprising, a tubular member defining an opening extending longitudinally for receiving said archwire, said member having inner surfaces for contacting said archwire, and a hook extending from said tubular member, said tubular member having a means on said inner surfaces for providing an anti-sliding condition such that upon crimping on said archwire said means engages said archwire thereby securely fixing said hook against sliding and rotating on said archwire.

* * * * *